US012672854B2

(12) United States Patent
    Takahashi

(10) Patent No.: US 12,672,854 B2
(45) Date of Patent: Jul. 7, 2026

(54) ULTRASOUND DIAGNOSIS APPARATUS AND ULTRASOUND DIAGNOSIS METHOD

(71) Applicant: CANON KABUSHIKI KAISHA, Tokyo (JP)

(72) Inventor: Hiroki Takahashi, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 8 days.

(21) Appl. No.: 18/589,189

(22) Filed: Feb. 27, 2024

(65) Prior Publication Data

US 2024/0285258 A1 Aug. 29, 2024

(30) Foreign Application Priority Data

Feb. 27, 2023 (JP) ................................. 2023-028832

(51) Int. Cl.
    *A61B 17/34* (2006.01)
    *A61B 8/00* (2006.01)
    *A61B 8/08* (2006.01)

(52) U.S. Cl.
    CPC ............ *A61B 8/488* (2013.01); *A61B 8/4455* (2013.01); *A61B 8/5207* (2013.01); *A61B 17/3403* (2013.01); *A61B 2017/3413* (2013.01)

(58) Field of Classification Search
    CPC ..... A61B 8/488; A61B 8/4455; A61B 8/5207; A61B 17/3403; A61B 2017/3413; A61B 8/0841
    See application file for complete search history.

(56) References Cited

U.S. PATENT DOCUMENTS

| | | | | |
|---|---|---|---|---|
| 6,233,526 | B1 * | 5/2001 | Cunningham | ........ G01F 1/8477 |
| | | | | 73/861.357 |
| 2013/0158390 | A1 * | 6/2013 | Tan | ........................ A61B 8/461 |
| | | | | 600/424 |
| 2017/0086793 | A1 * | 3/2017 | Sato | ..................... A61B 8/5207 |
| 2019/0209133 | A1 * | 7/2019 | Takahashi | ............ A61B 8/5207 |

(Continued)

FOREIGN PATENT DOCUMENTS

JP          2020-114282 A          7/2020

OTHER PUBLICATIONS

David Hope Simpson, et al., "Pulse Inversion Doppler: A New Method for Detecting Nonlinear Echoes from Microbubble Contrast Agents", IEEE Transactions on Ultrasonics, Ferroelectrics, and Frequency Control, vol. 46, No. 2, Mar. 1999 11 pages.

(Continued)

*Primary Examiner* — Amal Aly Farag
(74) *Attorney, Agent, or Firm* — Oblon, McClelland, Maier & Neustadt, L.L.P.

(57) ABSTRACT

An ultrasound diagnosis apparatus according to an embodiment includes transmitter and receiver circuitry and Doppler processing circuitry. The transmitter and receiver circuitry is configured to transmit ultrasound and receive an echo signal corresponding to the ultrasound. The Doppler processing circuitry is configured to perform principal component analysis of a first signal data string obtained from the echo signal, and is configured to extract a second signal data string from the first signal data string by reducing a predetermined Doppler frequency component, on the basis of at least one of an eigenvalue and an eigenvector obtained by the principal component analysis.

17 Claims, 13 Drawing Sheets

(56)                    References Cited

U.S. PATENT DOCUMENTS

2019/0357874 A1\*  11/2019  Yoshiara ............... G16H 50/30
2021/0338207 A1     11/2021  Takada et al.

OTHER PUBLICATIONS

Charles Tremblay-Darveau, et al., "Combined Perfusion and Doppler Imaging Using Plane-Wave Nonlinear Detection and Microbubble Contrast Agents", IEEE Transactions on Ultrasonics, Ferroelectrics, and Frequency Control, vol. 61, No. 12, Dec. 2014, 13 pages.

\* cited by examiner

Dir #  1  1  2  2  3  3  4  4  5  5  6  6  1  1  2  2  3  3  4  4  5  5  6  6

Dir #  1  2  3  4  5  6  1  2  3  4  5  6  1  2  3  4  5  6  1  2  3  4  5  6

Tx phase (deg):    0      0      0    ⋯

Frame #:    1      2      3    ⋯

Tx phase (deg):    0    180    0    ⋯

Frame #:    1      2      3    ⋯

EIGENVECTOR (THIRD EIGENORDER)

EIGENVECTOR (FOURTH EIGENORDER)

EIGENORDER COMPONENT NUMBER

RANKING BASED ON MAGNITUDE OF MEAN PHASE CHANGE

START

REDUCE EIGENORDER COMPONENT
HAVING LARGE MEAN PHASE
DIFFERENCE BETWEEN EIGENVECTORS
AND LARGE EIGENVALUE ~S330B

END

START

REDUCE EIGENORDER COMPONENT
HAVING LARGE MEAN PHASE
DIFFERENCE BETWEEN
EIGENVECTORS AND EIGENVALUE
LARGER THAN FIRST THRESHOLD
AND EIGENORDER COMPONENT
HAVING EIGENVALUE SMALLER
THAN SECOND THRESHOLD ~S330C

END

ULTRASOUND DIAGNOSIS APPARATUS AND ULTRASOUND DIAGNOSIS METHOD

CROSS-REFERENCE TO RELATED APPLICATIONS

This application is based upon and claims the benefit of priority from Japanese Patent Application No. 2023-028832, filed on Feb. 27, 2023; the entire contents of which are incorporated herein by reference.

FIELD

Embodiments disclosed in this specification are related to ultrasound diagnosis apparatuses and ultrasound diagnosis methods.

BACKGROUND

Movement detecting and imaging functions utilizing the Doppler phenomenon, such as color Doppler imaging, power Doppler imaging, and superb microvascular imaging (SMI), can be implemented by ultrasound diagnosis apparatuses. Improving detectability of low-velocity components to reduce echo components from surrounding body tissue and detect low-velocity targets is important in Doppler imaging for visualizing, for example, microscopic bloodstream and microscopic vibration of a puncture needle.

Decreasing the pulse repetition frequency (PRF) for the same spot is important in improving the detectability of low-velocity components. However, decrease in the PRF results in improvement of the detectability of low-velocity components but results in aliasing of Doppler information on body tissue other than the target and the resulting clutter interferes with the Doppler signal of the target. Therefore, in a case where the clutter component is higher in intensity than the signal component of the target, the signal of the target is unable to be visualized.

DETAILED DESCRIPTION

An ultrasound diagnosis apparatus provided, in one aspect of the present invention, includes transmitter and receiver circuitry and Doppler processing circuitry. The transmitter and receiver circuitry is configured to transmit ultrasound and receives an echo signal corresponding to the ultrasound. The Doppler processing circuitry is configured to perform principal component analysis of a first signal data string obtained from the echo signal, and configured to extract, on the basis of at least one of an eigenvalue and an eigenvector obtained by the principal component analysis, a second signal data string from the first signal data string, by reducing a predetermined Doppler frequency component.

First Embodiment

Embodiments of an ultrasound diagnosis apparatus and an ultrasound diagnosis method will hereinafter be described in detail while reference is made to the drawings.

Figure 1:
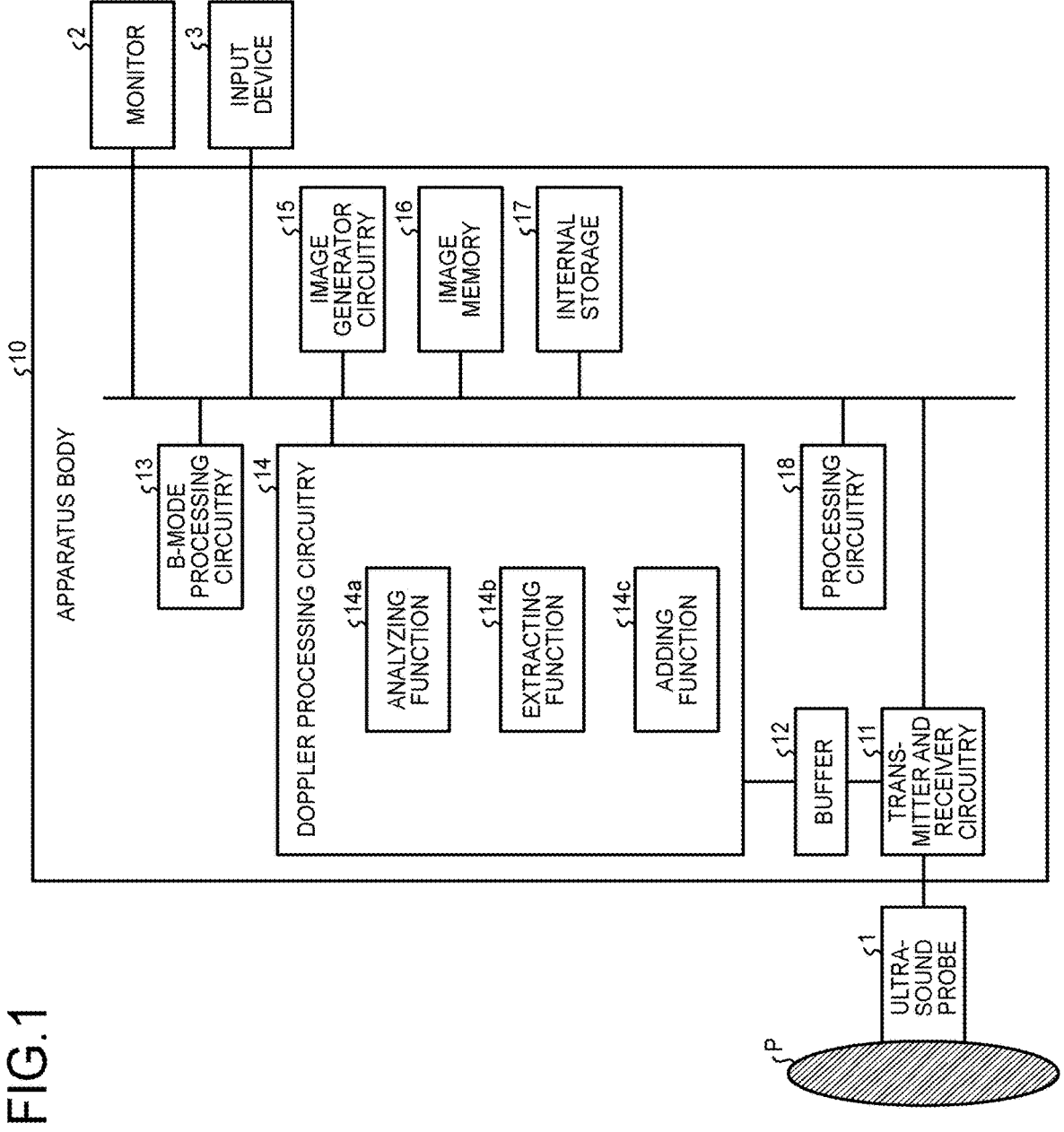
FIG. 1 is a diagram illustrating an example of a configuration of an ultrasound diagnosis apparatus according to an embodiment.

A configuration of an ultrasound diagnosis apparatus according to an embodiment will be described first. FIG. 1 is a block diagram illustrating an example of the configuration of the ultrasound diagnosis apparatus according to the embodiment. As exemplified by FIG. 1, the ultrasound diagnosis apparatus according to the embodiment has an ultrasound probe 1, a monitor 2, an input device 3, and an apparatus body 10.

The ultrasound probe 1 is connected to the apparatus body 10, for transmission and reception of ultrasound. The ultrasound probe 1 has, for example, plural piezoelectric transducers. These plural piezoelectric transducers generate ultrasound, on the basis of a drive signal supplied from transmitter and receiver circuitry 11 that the apparatus body 10 has. For example, the plural piezoelectric transducers transmit ultrasound to a subject P, the ultrasound having intensity corresponding to voltage applied from the transmitter and receiver circuitry 11. Furthermore, the plural piezoelectric transducers that the ultrasound probe 1 has receive reflected waves (echoes) from the subject P, converts the reflected waves received into an electric signal (a reflected wave signal), and transmits the reflected wave signal to the apparatus body 10. The ultrasound probe 1 also has, for example, matching layers provided on the piezoelectric transducers, and a backing material that prevents propagation of ultrasound backward from the piezoelectric transducers. The ultrasound probe 1 is detachably connected to the apparatus body 10.

In response to transmission of ultrasound from the ultrasound probe 1 to the subject P, the ultrasound transmitted is: successively reflected by acoustic impedance discontinuities in tissue in the body of the subject P; and received as reflected waves by the plural piezoelectric transducers that the ultrasound probe 1 has. The amplitudes of the reflected waves received are dependent on the acoustic impedance differences at the discontinuities where the ultrasound is reflected.

The embodiment is applicable to a 1D array probe for two-dimensionally scanning the subject P or a mechanical 4D probe or 2D array probe for three-dimensionally scanning the subject P.

The input device 3 is implemented by, for example, a mouse, a keyboard, a button, a panel switch, a touch command screen, a foot switch, a trackball, and/or a joystick. The input device 3 receives various setting requests from an operator or operators of the ultrasound diagnosis apparatus and transfers the various setting requests received, to the apparatus body 10.

The monitor 2 displays a graphical user interface (GUI) for an operator of the ultrasound diagnosis apparatus to input various setting requests by using the input device 3 and displays, for example, an ultrasound image represented by ultrasound image data generated at the apparatus body 10. The monitor 2 is implemented by, for example, a liquid crystal monitor or a cathode ray tube (CRT) monitor.

The apparatus body 10 is an apparatus that generates ultrasound image data on the basis of a reflected wave signal transmitted from the ultrasound probe 1. The apparatus body 10 illustrated in FIG. 1 is an apparatus that is capable of generating two-dimensional ultrasound image data on the basis of a two-dimensional reflected wave signal and generating three-dimensional ultrasound image data on the basis of a three-dimensional reflected wave signal.

The apparatus body 10 has, as exemplified by FIG. 1, the transmitter and receiver circuitry 11, a buffer 12, B-mode processing circuitry 13, Doppler processing circuitry 14, image generator circuitry 15, an image memory 16, an internal storage 17, and processing circuitry 18.

The transmitter and receiver circuitry 11 controls ultrasound scanning implemented by the ultrasound probe 1 on the basis of an instruction from the processing circuitry 18 described later. Ultrasound scanning refers to, for example, transmission and reception of ultrasound. The transmitter and receiver circuitry 11 has a pulse generator, transmission delay circuitry, and a pulser, for example, and supplies drive signals to the ultrasound probe 1. The pulse generator repeatedly generates a rate pulse for forming transmitted ultrasound, at a predetermined pulse repetition frequency (PRF). Furthermore, the transmission delay circuitry adds delay times respectively for the piezoelectric transducers to the respective rate pulses generated by the pulse generator, the delay times being required to converge the ultrasound generated by the ultrasound probe 1 into a beam form and to determine the transmission directivity. Furthermore, the pulser applies a drive signal to the ultrasound probe 1 at a time based on a rate pulse. That is, by varying the delay times to be added to the respective rate pulses, the transmission delay circuitry optionally adjusts the transmission directions of ultrasound transmitted from surfaces of the piezoelectric transducers.

For example, the transmitter and receiver circuitry 11 causes the ultrasound probe 1 to execute ultrasound scanning to collect a data string over frames as a Doppler data string, through control by the processing circuitry 18. For example, the ultrasound probe 1 and the transmitter and receiver circuitry 11 collect reflected wave data from the same position over plural frames in a temporal direction to thereby collect a data string of reflected wave data on the same position.

Furthermore, the transmitter and receiver circuitry 11 has, for example, amplifier circuitry, an analog/digital (A/D) converter, reception delay circuitry, an adder, and quadrature detection circuitry, and generates reflected wave data by performing various types of processing of a reflected wave signal transmitted from the ultrasound probe 1. The transmitter and receiver circuitry 11 then stores the generated reflected wave data into the buffer 12. The amplifier circuitry performs gain correction processing by amplifying the reflected wave signal for each channel. The A/D converter performs A/D conversion of the reflected wave signal that has been subjected to the gain correction processing. The reception delay circuitry adds, to the digital data, a reception delay time required for determination of the reception directivity. The adder performs addition processing of the reflected wave signal that has been added with the reception delay time by the reception delay circuitry. Through the addition processing by the adder, a reflection component from a direction corresponding to the reception directivity of the reflected wave signal is enhanced. The process of performing phase adjustment by delaying reception of each of the reflected wave signals from the elements and performing the addition is also referred to as a phasing and adding process or a beamforming process.

The quadrature detection circuitry converts an output signal from the adder into an in-phase signal (I signal) and a quadrature-phase signal (Q-signal) of a baseband. The quadrature detection circuitry then stores the I signal and Q signal (hereinafter, referred to as "IQ signals") as reflected wave data, into the buffer 12.

The buffer 12 is a memory that temporarily stores reflected wave data generated by the transmitter and receiver circuitry 11. Specifically, the buffer 12 stores reflected wave data corresponding to a few frames or reflected wave data corresponding to a few volumes. For example, the buffer 12 is a first-in/first-out (FIFO) memory and stores reflected wave data corresponding to a predetermined number of frames under control by the transmitter and receiver circuitry 11. In a case where reflected wave data corresponding to one frame are newly generated by the transmitter and receiver circuitry 11, for example, the buffer 12 then stores, under control by the transmitter and receiver circuitry 11, the newly generated reflected wave data corresponding to the one frame by discarding the oldest reflected wave data corresponding to one frame, the oldest reflected wave data having been generated earliest. For example, the buffer 12 is implemented by a semiconductor memory device, such as a random access memory (RAM) or a flash memory.

The B-mode processing circuitry 13 and the Doppler processing circuitry 14 are signal processing units that perform various types of signal processing of reflected wave data generated from a reflected wave signal by the transmitter and receiver circuitry 11. The B-mode processing circuitry 13 and the Doppler processing circuitry 14 are implemented by, for example, a processor. The B-mode processing circuitry 13 reads reflected wave data from the buffer 12, performs logarithmic amplification, envelope detection processing, and logarithmic compression, for example, of the reflected wave data read, to generate data (B-mode data) having signal intensities of plural sample points represented by luminance.

The Doppler processing circuitry 14 reads reflected wave data from the buffer 12 and performs frequency analysis of the reflected wave data read, to estimate movement information based on the Doppler effect of a moving object in a scan range and generate data (Doppler data) representing the movement information estimated. For example, the Doppler processing circuitry 14 estimates movement information on a moving object at each of plural sample points, the movement information being, for example, a mean velocity, a mean variance value, and a mean power value, and generates Doppler data representing the movement information estimated. The moving object herein is, for example, bloodstream, tissue of a cardiac wall, or a contrast agent.

The ultrasound diagnosis apparatus according to the embodiment is capable of executing the color Doppler method also referred to as the color flow mapping (CFM) method, by using the above described functions of the Doppler processing circuitry 14. In this CFM method, ultrasound transmission and reception are performed a plural number of times on plural scan lines. In the CFM method, a bloodstream signal resulting from bloodstream is extracted by reducing a signal (a clutter signal) resulting from still tissue or slow-moving tissue, by filtering a data string for the same position through a moving target indicator (MTI) filter. For example, in response to input of a data string of reflected wave data on the same position to an MTI filter, the MTI filter outputs a bloodstream signal having reduced clutter and dominated by a bloodstream component. An adaptive principal component analysis filter that changes the coefficients according to an input signal is used, for example, as the MTI filter.

As exemplified by FIG. 1, the Doppler processing circuitry 14 has an analyzing function 14*a*, an extracting function 14*b*, and an adding function 14*c*. Each of processing functions executed by the Doppler processing circuitry 14 having the analyzing function 14*a*, the extracting function 14*b*, and the adding function 14*c* has been recorded in the internal storage 17 in the form of a program that is able to be executed by a computer. The Doppler processing circuitry 14 reads each program from the internal storage 17 and implements a function corresponding to the read program by executing the read program. In other words, the Doppler processing circuitry 14 that has read the programs has the functions illustrated in the Doppler processing circuitry 14 in FIG. 1.

Various processes executed by the analyzing function 14*a*, the extracting function 14*b*, and the adding function 14*c* will be described later. The analyzing function 14*a*, the extracting function 14*b*, and the adding function 14*c* are respectively examples of an analysis unit, an extraction unit, and an addition unit. The transmitter and receiver circuitry 11 is an example of a transmission and reception unit.

The image generator circuitry 15 generates ultrasound image data from data generated by the B-mode processing circuitry 13 and Doppler processing circuitry 14.

Generally, the image generator circuitry 15 generates ultrasound image data for display by converting (scan-converting) a scan line signal string from ultrasound scanning, into a scan line signal string having a video format typical of television, for example. Specifically, the image generator circuitry 15 generates ultrasound image data for display, by performing coordinate transformation according to the mode of the ultrasound scanning by the ultrasound probe 1. Furthermore, the image generator circuitry 15 performs various types of image processing other than the scan-converting, by using, for example, plural image frames that have been scan-converted, the various types of image processing including, for example, image processing (smoothing processing) for regenerating a mean luminance value image and image processing (edge enhancement processing) using a differential filter within the images. In addition, the image generator circuitry 15 combines the ultrasound image data with textual information on various parameters, scales, and body marks, for example.

The image memory 16 is a memory that stores image data for display, the image data having been generated by the image generator circuitry 15. Furthermore, the image memory 16 is also capable of storing data generated by the B-mode processing circuitry 13 and Doppler processing circuitry 14.

The internal storage 17 stores: a control program for performing ultrasound transmission and reception, image processing, and display processing; and various data, such as diagnostic information (for example, patient IDs and observations by doctors), diagnostic protocols, and various body marks. Furthermore, the internal storage 17 is used, as required, for storage of image data stored in the image memory 16, for example. In addition, data stored in the internal storage 17 are able to be transferred to an external device via an interface not illustrated in the drawings. The internal storage 17 is also capable of storing data transferred from an external device via an interface not illustrated in the drawings. For example, the internal storage 17 is implemented by: a semiconductor memory device, such as a flash memory; a hard disk; or an optical disk.

The processing circuitry 18 controls the overall processing by the ultrasound diagnosis apparatus. Specifically, the processing circuitry 18 controls processing by the transmitter and receiver circuitry 11, the B-mode processing circuitry 13, the Doppler processing circuitry 14, and the image generator circuitry 15, on the basis of various setting requests input by an operator via the input device 3 and various control programs and various data read from the internal storage 17. For example, by controlling the ultrasound probe 1 via the transmitter and receiver circuitry 11, the processing circuitry 18 controls the ultrasound scanning.

Background related to the embodiment will be described next.

Movement detecting and imaging functions utilizing the Doppler phenomenon, such as color Doppler imaging, power Doppler imaging, and superb microvascular imaging (SMI), can be implemented by ultrasound diagnosis apparatuses. Improving detectability of low-velocity components to reduce echo components from surrounding body tissue and detect low-velocity targets is important in Doppler imaging for visualizing, for example, microscopic bloodstream and microscopic vibration of a puncture needle.

Decreasing the pulse repetition frequency (PRF) for the same spot is important in improving the detectability of low-velocity components. However, decrease in the PRF results in improvement of the detectability of low-velocity components but results in aliasing of Doppler information on body tissue other than the target and the resulting clutter interferes with the Doppler signal of the target. Therefore, in a case where the clutter component is higher in intensity than the signal component of the target, the signal of the target is unable to be visualized.

Utilizing harmonic components may be considered as a method that may decrease the PRF and reduce the clutter component. A visualization method utilizing harmonic components is called harmonic imaging and widely implemented as functions of ultrasound diagnosis apparatuses, and examples of this visualization method include tissue harmonic imaging (THI) of visualizing harmonic components accumulated as ultrasound propagates through body tissue and contrast harmonic imaging (CHI) of visualizing harmonic components generated from a contrast agent. Mechanisms of harmonic generation in THI and CHI differ from each other, but THI and CHI are the same in that they are used to reduce undesired components in visualization, that is, clutter components and to enhance desired components by utilization of: a characteristic of harmonic components, the characteristic being that the spread of the sound field is small for harmonic components; and the fact that intense echoes are obtained from targets having nonlinearity, such as a contrast agent. Examples of a means for extracting harmonic components include a method of obtaining a harmonic frequency band by applying frequency filtering to received echoes, a method (pulse inversion) of adding a received signal obtained by transmission of a waveform that has been phase-modulated in the same direction by 180 degrees, and a method (amplitude modulation) of adding and subtracting a received signal obtained by transmission of a waveform that has been modulated in amplitude in the same direction. The pulse inversion Doppler method is also known as a means for extracting harmonic components of a moving object. In the pulse inversion Doppler method, transmitter and receiver circuitry 11 performs imaging by transmitting a combination of ultrasound transmitted in a certain phase and ultrasound transmitted after being phase-modulated by 180 degrees and extracting harmonic components on the basis of the amount of Doppler shift in a received signal obtained.

Two types of methods, line-by scanning of inverting the phase of transmitted ultrasound in every line to be scanned and frame-by scanning of transmitting plural lines together in the same phase in frame units and inverting the phase of the transmitted ultrasound in every frame, may be considered for implementation of the pulse inversion Doppler method.

Figure 2:
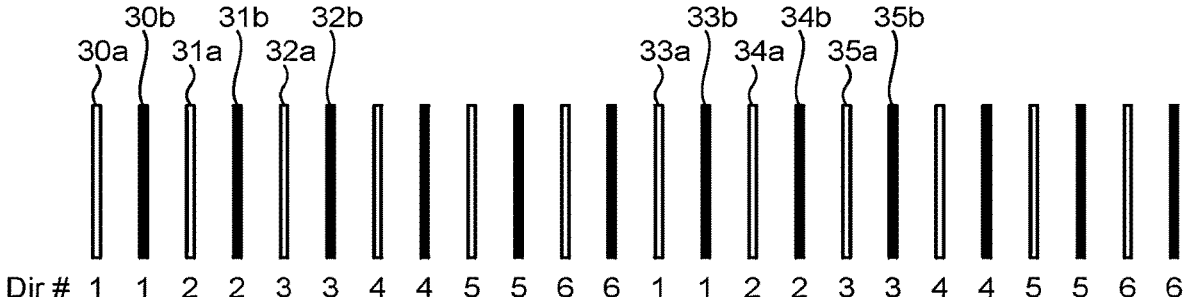
FIG. 2 is a diagram illustrating an example of ultrasound transmission in line-by scanning.

The line-by scanning and the frame-by scanning will now be described by use of FIG. 2 and FIG. 3. FIG. 2 is a diagram illustrating ultrasound transmission using the line-by scanning and FIG. 3 is a diagram illustrating ultrasound transmission using the frame-by scanning.

In a case where the pulse inversion Doppler method is implemented by use of the line-by scanning as illustrated in FIG. 2, the transmitter and receiver circuitry 11 performs ultrasound transmission by inverting the phase of the transmitted ultrasound in every line as illustrated in FIG. 2, for example. For example, the transmitter and receiver circuitry 11 performs ultrasound transmission 30a in a first phase for a line corresponding to a first direction, performs ultrasound transmission 30b in a second phase for the line corresponding to the first direction, the second phase being opposite to the first phase, performs ultrasound transmission 31a in the first phase for a line corresponding to a second direction, performs ultrasound transmission 31b in the second phase for the line corresponding to the second direction, performs ultrasound transmission 32a in the first phase and ultrasound transmission 32b in the second phase, for a line corresponding to a third direction, and performs ultrasound transmission similarly for a fourth direction to a sixth direction. The ultrasound transmission in these six directions are included in one frame.

Subsequently, the transmitter and receiver circuitry 11 performs ultrasound transmission 33a in the first phase again and ultrasound transmission 33b in the second phase, for the line corresponding to the first direction, performs ultrasound transmission 34a in the first phase and ultrasound transmission 34b in the second phase for the line corresponding to the second direction, performs ultrasound transmission 35a in the first phase and ultrasound transmission 35b in the second phase, for the line corresponding to the third direction, and performs ultrasound transmission similarly for the fourth direction to the sixth direction. The line-by scanning is lower in frame rate than the frame-by scanning.

Figure 3:
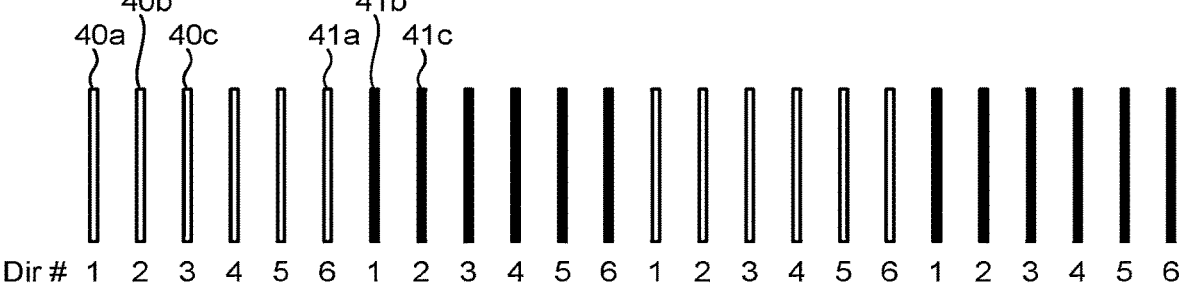
FIG. 3 is a diagram illustrating an example of ultrasound transmission in frame-by scanning.

By contrast, as illustrated in FIG. 3, in a case where the pulse inversion Doppler method is implemented by the frame-by scanning, the transmitter and receiver circuitry 11 transmits ultrasound in the same phase, a first phase, in plural directions within one frame, and thereafter transmits ultrasound in a second phase opposite to the first phase in the plural directions. Specifically, the transmitter and receiver circuitry 11 executes ultrasound transmission 40a, 40b, and 40c in the same phase, the first phase, in a first direction to a sixth direction, and thereafter executes ultrasound transmission 41a, 41b, and 41c in the second phase opposite to the first phase in the first direction to the sixth direction.

In a case where the transmitter and receiver circuitry 11 implements the pulse inversion Doppler method by ultrasound transmission through the frame-by scanning as described above, the frame rate is able to be maintained. Therefore, ultrasound transmission by the frame-by scanning is considered to be desirable.

However, adopting the frame-by scanning reduces the PRF, results in improvement of the detectability for low-velocity components, but also results in aliasing of Doppler information on body tissue other than the target and the resulting clutter interferes with the Doppler signal of the target. Therefore, a means for adequately removing the clutter component needs to be devised.

On the basis of such background, the ultrasound diagnosis apparatus according to the embodiment includes the transmitter and receiver circuitry 11 and the Doppler processing circuitry 14. The transmitter and receiver circuitry 11 transmits ultrasound and receives an echo signal corresponding to the ultrasound. The Doppler processing circuitry 14 performs, by means of the analyzing function 14a, principal component analysis of a first signal data string obtained from the echo signal. The Doppler processing circuitry 14 extracts a second signal data string from the first signal data string, by reducing a predetermined Doppler frequency component in the first signal data string, on the basis of at least one of an eigenvalue and an eigenvector obtained by the principal component analysis. A Doppler frequency referred to herein is a frequency of a signal amplitude in a frame direction (also called a slow time direction) in a signal data string.

Furthermore, an ultrasound diagnosis method according to the embodiment includes transmitting ultrasound, receiving an echo signal corresponding to the ultrasound, performing principal component analysis of a first signal data string obtained from the echo signal, and extracting a second signal data string from the first signal data string, by reducing a predetermined Doppler frequency component in the first signal data string on the basis of at least one of an eigenvalue and an eigenvector obtained by the principal component analysis.

Clutter is thereby able to be reduced adequately with the imaging frame rate maintained high and the detectability of low-velocity components is thus able to be improved.

Figure 4:
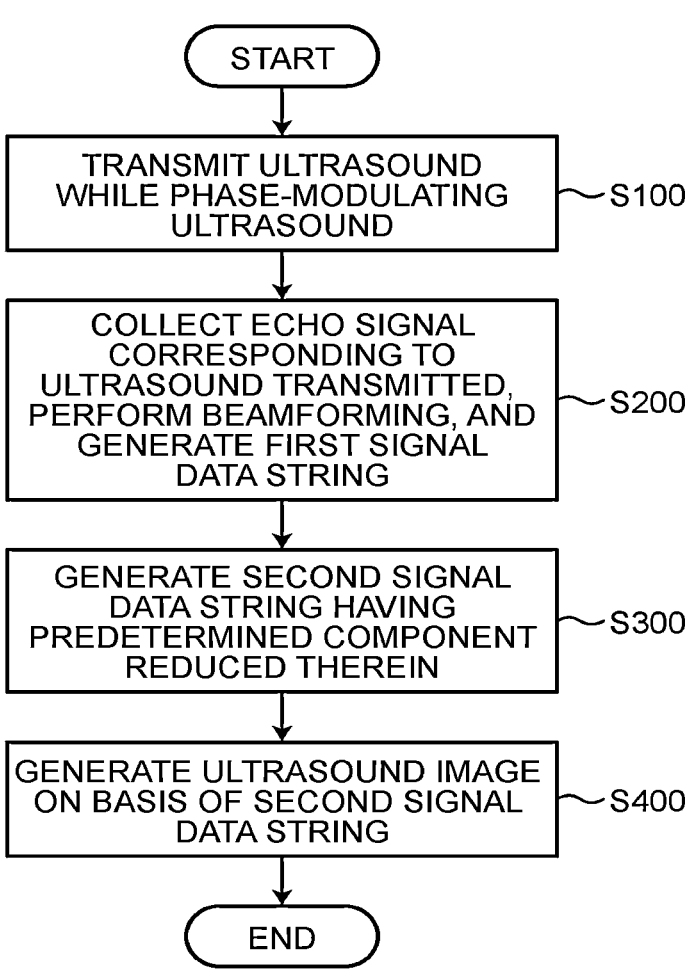
FIG. 4 is a flowchart illustrating an example of a flow of a process implemented by an ultrasound diagnosis apparatus according to a first embodiment.

A process performed by the ultrasound diagnosis apparatus according to a first embodiment will be described by use of FIG. 4, while reference is made as appropriate to FIG. 5 to FIG. 12. FIG. 4 is a flowchart illustrating an example of a flow of the process performed by the ultrasound diagnosis apparatus according to the first embodiment.

Firstly, at Step S100, the transmitter and receiver circuitry 11 transmits ultrasound while phase-modulating the ultrasound. For example, while phase-modulating the ultrasound by 180 degrees, the transmitter and receiver circuitry 11 transmits the ultrasound by the pulse inversion Doppler method using the frame-by scanning.

Subsequently, at Step S200, the transmitter and receiver circuitry 11 receives an echo signal corresponding to the ultrasound transmitted, performs beamforming, and generates a first signal data string S.

Specifically, the transmitter and receiver circuitry 11 collects the echo signal corresponding to the ultrasound transmitted, performs the beamforming, and thereby generates an echo signal value s(i, j, k) after the beamforming. Herein, i is a lateral direction, j is an index indicating a position in an axial direction, and k is a frame number. The echo signal value s(i, j, k) is able to be represented by s(n, k) where $N_j$ is the number of samples in the axial direction. Here, $n=i \times N_j + j$ holds. In this example, an echo signal of a frame number k has been obtained by transmission of a waveform in a reference phase and an echo signal of a frame number k+1 has been obtained by transmission of a waveform phase-modulated by 180 degrees.

The echo signal value s(n, k) after the beamforming is able to be represented by a matrix as expressed by Equation (1) below.

$$S = \begin{pmatrix} s(1,1) & \cdots & s(n,1) & \cdots & s(N_n,1) \\ & \ddots & & & \\ \vdots & & s(n,k) & & \vdots \\ & & & \ddots & \\ & & & & s(N_n, N_k) \end{pmatrix} \quad (1)$$

In Equation (1), $N_n$ is the largest value of n and $N_k$ is the number of frames. A matrix S in Equation (1) is an example of the first signal data string S. The first signal data string S is transmitted to the buffer 12, and the Doppler processing circuitry 14 obtains the first signal data string S from the buffer 12.

Data structures of ultrasound data collected by an ultrasound diagnosis apparatus in a comparative example and the ultrasound diagnosis apparatus in the first embodiment will now be described by use of FIG. 5 and FIG. 6.

Figure 5:
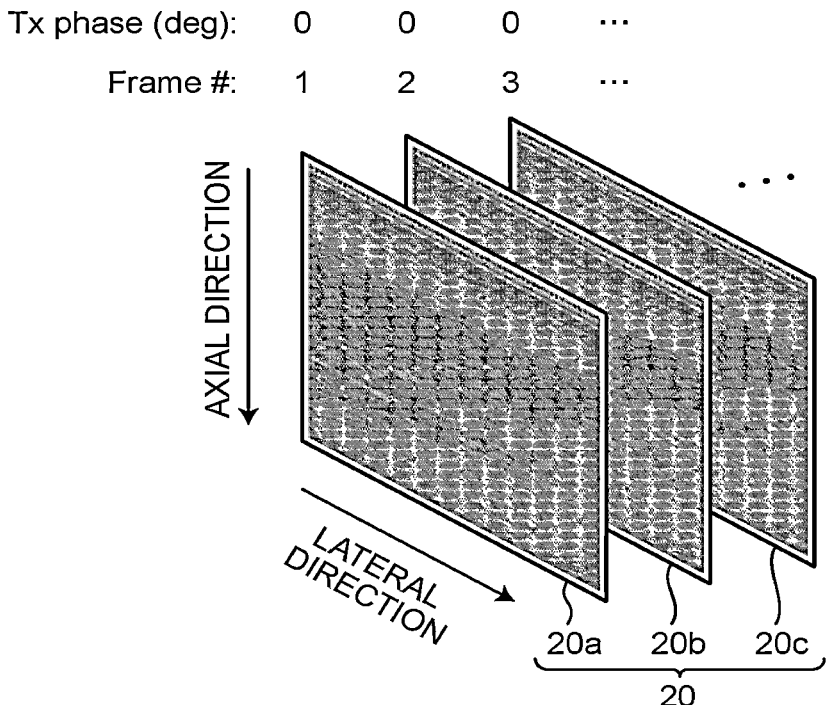
FIG. 5 is a diagram illustrating an example of a data structure of ultrasound data collected by an ultrasound diagnosis apparatus according to a comparative example.

FIG. 5 is a diagram illustrating an example of a data structure of a first signal data string collected by the ultrasound diagnosis apparatus according to the comparative example. In the comparative example, a first signal data string S includes data corresponding to transmitted ultrasound of the same phase, such as data 20a related to a first frame corresponding to ultrasound transmitted in a transmission phase of 0 degrees; data 20b related to a second frame corresponding to ultrasound transmitted in the transmission phase of 0 degrees; and data 20c related to a third frame corresponding to ultrasound transmitted in the transmission phase of 0 degrees.

Figure 6:
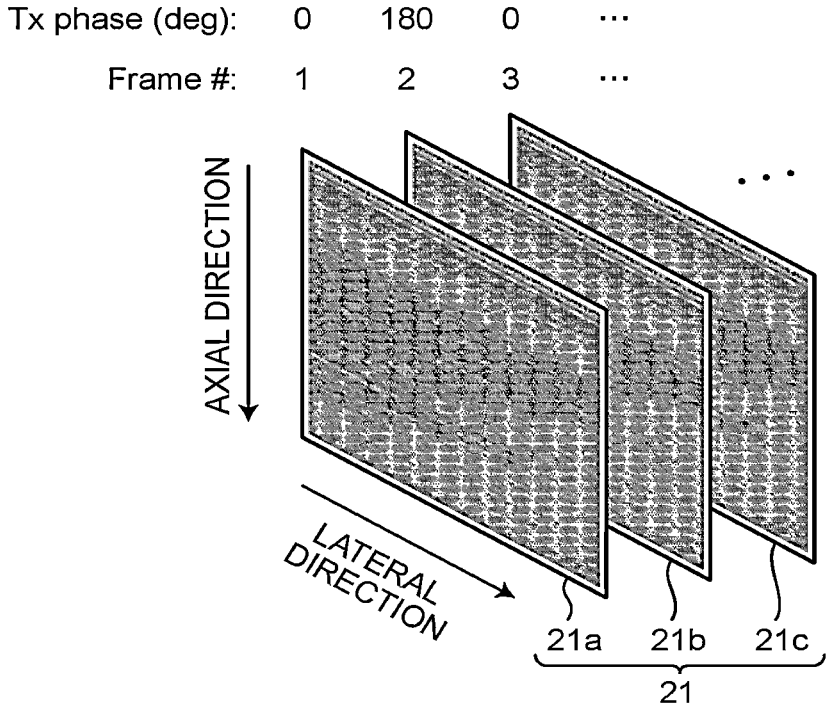
FIG. 6 is a diagram illustrating an example of a data structure of a first signal data string collected by the ultrasound diagnosis apparatus according to the first embodiment.

FIG. 6 is a diagram illustrating an example of a data structure of a first signal data string collected by the ultrasound diagnosis apparatus according to the first embodiment. In the first embodiment, the first signal data string S includes data corresponding to transmitted ultrasound that has been inverted in phase in every frame, such as data 21a related to a first frame corresponding to ultrasound transmitted in a transmission phase of 0 degrees, data 21b related to a second frame corresponding to ultrasound transmitted in a transmission phase of 180 degrees, and data 21c related to a third frame corresponding to ultrasound transmitted in a transmission phase of 0 degrees.

As illustrated in FIG. 4, subsequently, at Step S300, the Doppler processing circuitry 14 generates, by means of the analyzing function 14a and the extracting function 14b, a second signal data string having a predetermined component reduced therein, from the first signal data string S. Specifically, the Doppler processing circuitry 14 performs, by means of the analyzing function 14a, principal component analysis of the first signal data string S obtained from the echo signal. The Doppler processing circuitry 14 extracts, by means of the extracting function 14b, a second signal data string Y from the first signal data string S, by reducing a predetermined Doppler frequency component in the first signal data string S, on the basis of at least one of an eigenvalue and an eigenvector obtained by eigenvalue expansion.

Figure 7:
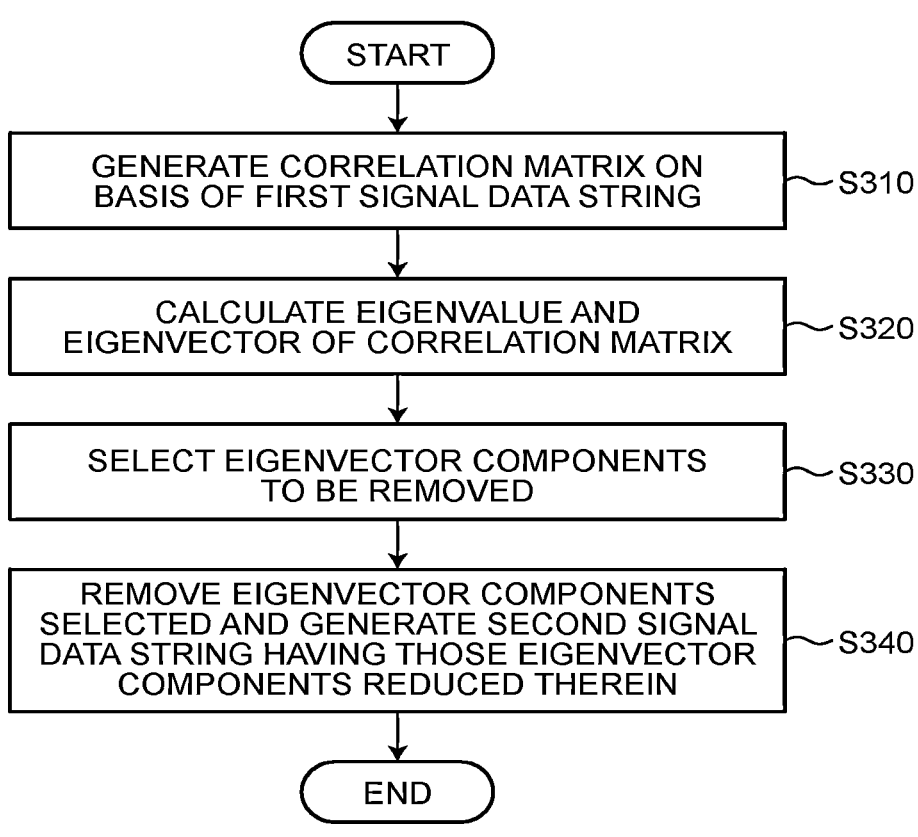
FIG. 7 is a flowchart illustrating a process at Step S300 in FIG. 4, in more detail.

This process at Step S300 will now be described in more detail by use of FIG. 7. FIG. 7 is a flowchart illustrating the process at Step S300 in FIG. 4 in more detail.

Firstly, at Step S310, the Doppler processing circuitry 14 generates, by means of the analyzing function 14a, a correlation matrix R as expressed by Equation (2) below, on the basis of the first signal data string S.

$$R = SS^H \quad (2)$$

In Equation (2), a symbol H represents a complex conjugate transpose.

Subsequently, at Step S320, the Doppler processing circuitry 14 calculates, by means of the analyzing function 14a, an eigenvalue and an eigenvector of the correlation matrix R calculated at Step S310.

FIG. 8A to FIG. 8D illustrate examples of eigenvectors calculated by the Doppler processing circuitry 14, that is, principal component vectors of an echo signal string obtained by phase modulation scanning.

Figures 8A, 8B:
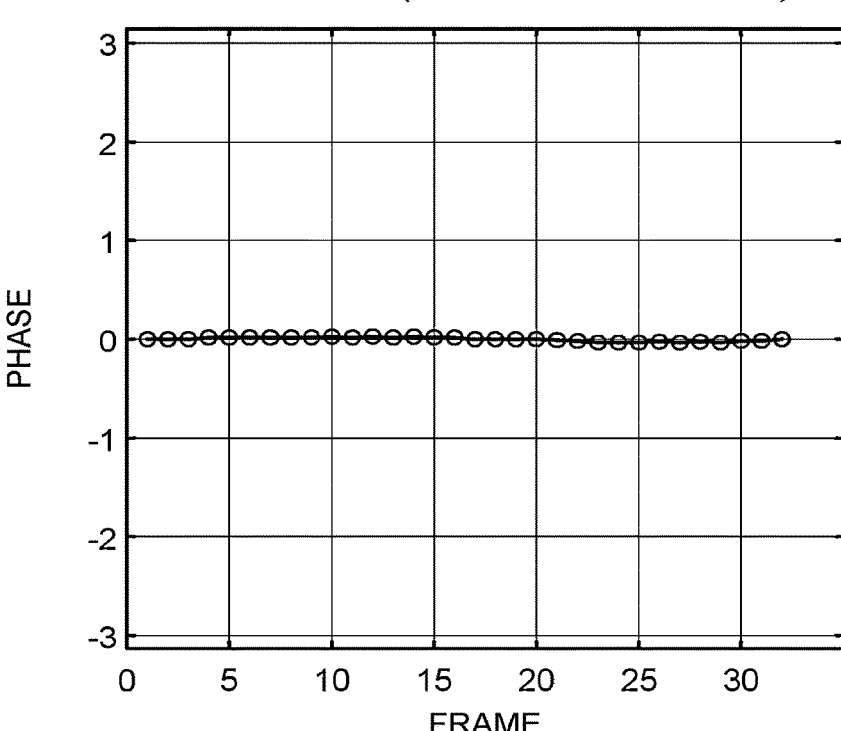
FIG. 8A is a diagram illustrating a process implemented by the ultrasound diagnosis apparatus according to the first embodiment.
FIG. 8B is a diagram illustrating a process implemented by the ultrasound diagnosis apparatus according to the first embodiment.
Figure 8C:
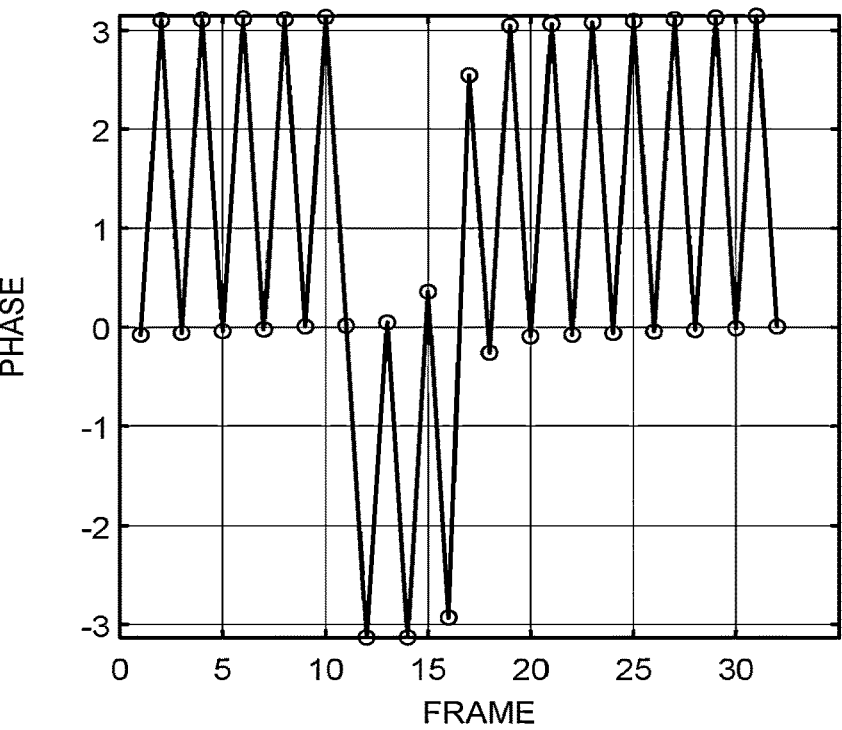
FIG. 8C is a diagram illustrating a process implemented by the ultrasound diagnosis apparatus according to the first embodiment.
Figure 8D:
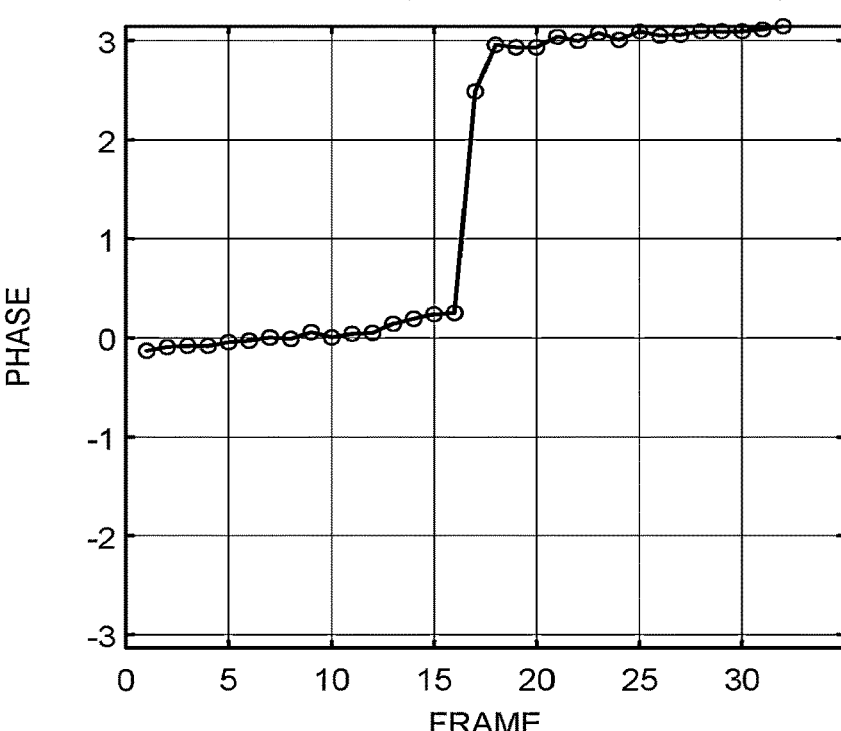
FIG. 8D is a diagram illustrating a process implemented by the ultrasound diagnosis apparatus according to the first embodiment.

FIG. 8A, FIG. 8B, FIG. 8C, and FIG. 8D respectively illustrate principal component vectors of a first eigenorder, a second eigenorder, a third eigenorder, and a fourth eigenorder. The principal component vector of the first eigenorder in FIG. 8A is a principal component vector representing the most dominant contribution to the echo signal string. Furthermore, the principal component vectors of the first eigenorder and third eigenorder are principal component vectors corresponding to a fundamental wave and the principal component vectors of the second eigenorder and fourth eigenorder are principal component vectors corresponding to harmonics.

At Step S320, the Doppler processing circuitry 14 calculates, by means of the analyzing function 14a, an eigenvalue and an eigenvector of the correlation matrix R calculated at Step S310, by eigenvalue expansion of the first signal data string S in the frame direction. Furthermore, the Doppler processing circuitry 14 calculates, by means of the analyzing function 14a, a coefficient for the expansion of the signal data string S with the eigenvector calculated at Step S310.

Subsequently, at Step S330, the Doppler processing circuitry 14 selects, by means of the extracting function 14b, an eigenvector component to be removed (reduced) at Step S340 described later.

Figure 9:
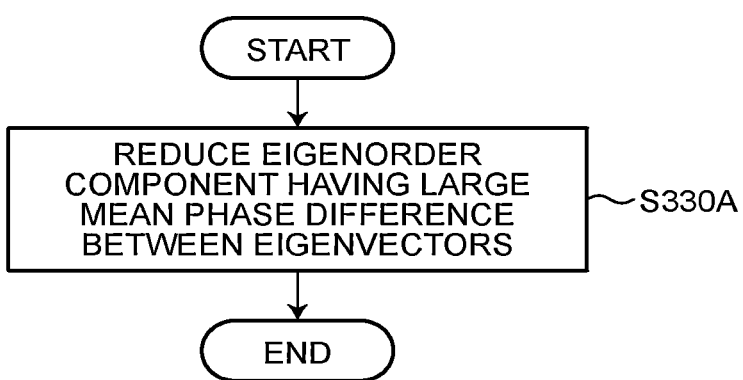
FIG. 9 is a flowchart illustrating a process at Step S330 in FIG. 7 in the first embodiment.

FIG. 9 is a flowchart illustrating an example of the process at Step S330. That is, at Step S330A, the Doppler processing circuitry 14 executes the process of Step S330 in FIG. 7 by extracting, by means of the extracting function 14b, a second signal data string from the first signal data string S, on the basis of mean phase differences in eigenvectors.

The significance of selecting an eigenvector component to be reduced on the basis of mean phase differences in eigenvectors is thought to be in that a phase difference in a fundamental wave component is dependent on a transmission phase and becomes 180 degrees in 180-degree phase modulation transmission but phase differences in second-order or higher even-order harmonics become 2 (order)×180 degrees=360 degrees (=0 degrees) and the difference due to the transmission phase is thereby offset. This means that if a fundamental wave component in an echo signal data string is observed in a frame direction, the fundamental wave component appears as a periodic fluctuation component. The phase difference in a fundamental wave component is thought to be larger than the phase difference in a transmitted wave component. Therefore, reducing an eigenvector component having a large mean phase change enables the fundamental wave component to be removed and the second-order or higher even-order harmonic component to be extracted. A clutter component resulting from spread of the sound field is thought to be included more in the fundamental wave component, and performing such a process is thus thought to enable the clutter to be removed. That is, at Step S330 and Step S340, the Doppler processing circuitry 14 is able to extract, by means of the extracting function 14b, the second signal data string Y by extracting a harmonic component from the first signal data string S. For example, the Doppler processing circuitry 14 is able to extract a blood-stream signal as the second signal data string Y by extracting, by means of the extracting function 14b, a harmonic component from the first signal data string S.

In an example where an eigenvector component to be reduced is selected on the basis of mean phase differences in eigenvectors, the Doppler processing circuitry 14 selects as the eigenvector to be reduced at Step S340, by means of the extracting function 14b, an eigenvector having a mean phase difference larger than a threshold. Furthermore, in another example, by means of the extracting function 14b, the Doppler processing circuitry 14 rearranges eigenvectors in descending order of mean phase change and selects the top N eigen vectors having larger mean phase differences, where N is a natural number, the N eigen vectors being eigen vectors to be reduced at Step S340.

Figure 10:
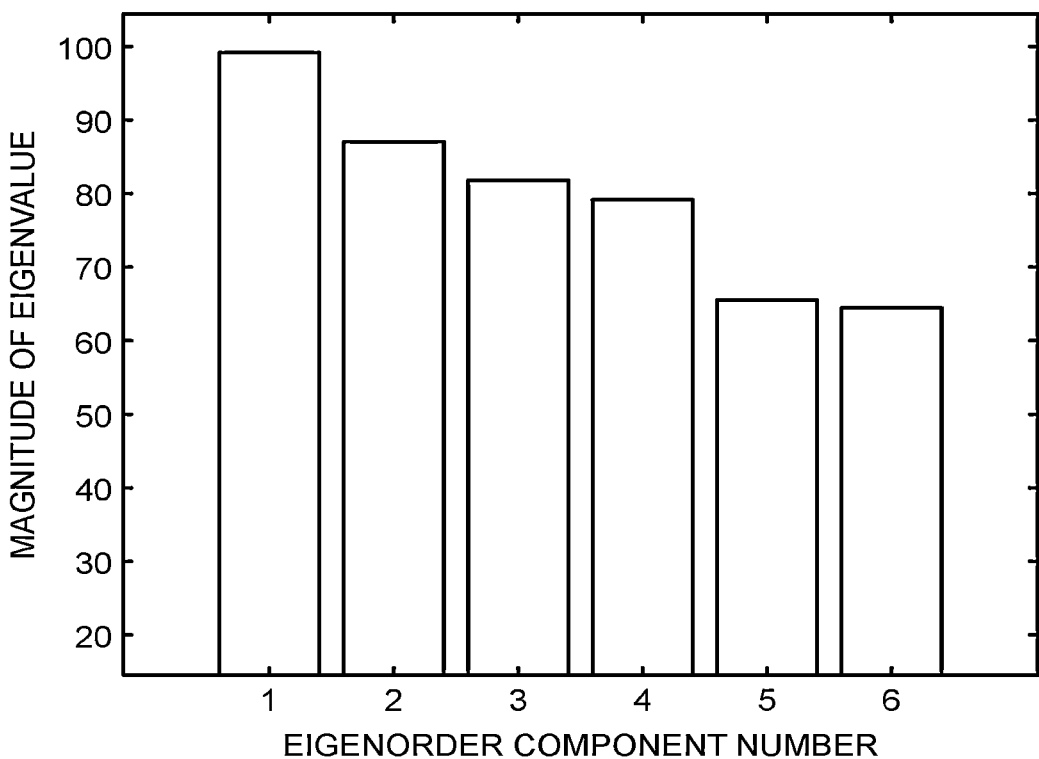
FIG. 10 is a diagram illustrating a process implemented by the ultrasound diagnosis apparatus according to the first embodiment.
Figure 11:
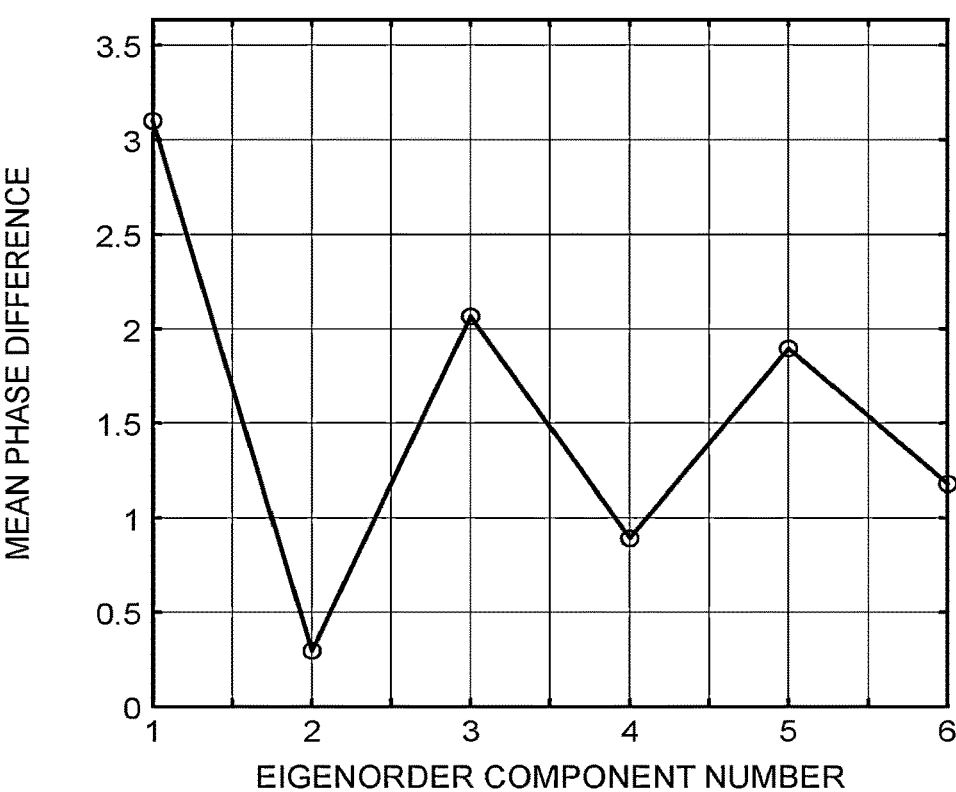
FIG. 11 is a diagram illustrating a process implemented by the ultrasound diagnosis apparatus according to the first embodiment.

FIG. 10 illustrates an example of magnitude of eigenvalues corresponding to eigenvectors. The smaller the number for an eigenorder component is, the larger the magnitude of the eigenvalue corresponding to the eigenvector of the eigenorder component. The Doppler processing circuitry 14 calculates, by means of the extracting function 14b, mean phase differences in eigenvectors of eigenorder components. FIG. 11 illustrates mean phase differences calculated for eigenvectors of eigenorder components. For example, in the example of FIG. 11, mean phase differences in eigenvectors corresponding to first, third, fifth, and sixth eigenorder components are larger than mean phase differences in eigenvectors corresponding to the other eigenorder components.

Figure 12:
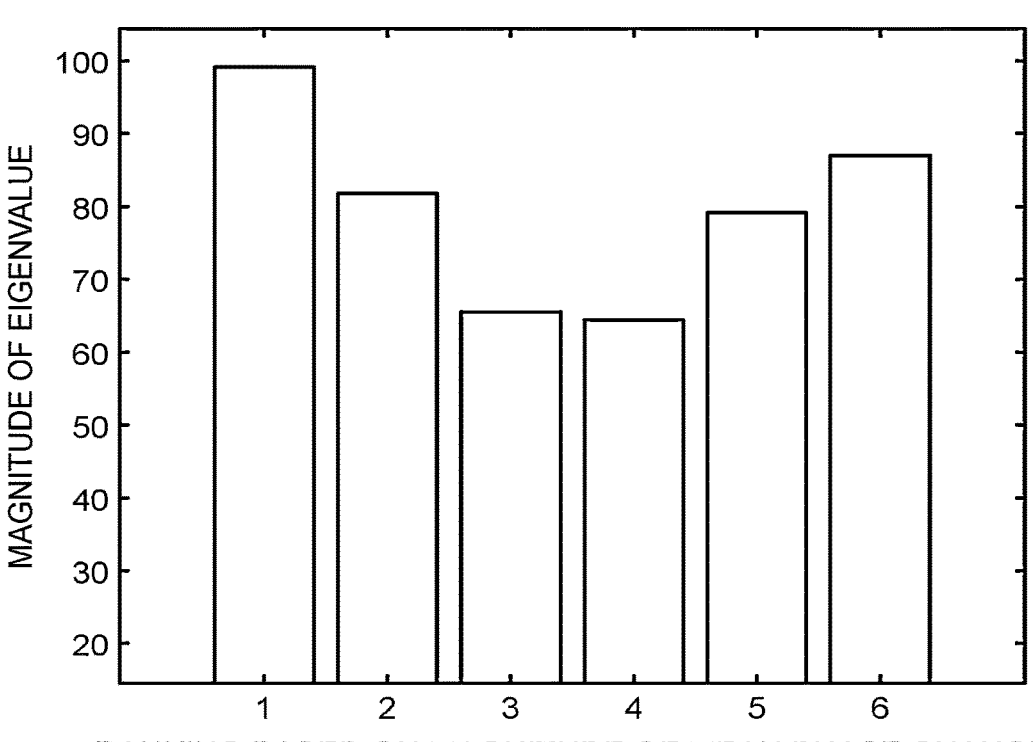
FIG. 12 is a diagram illustrating a process implemented by the ultrasound diagnosis apparatus according to the first embodiment.

FIG. 12 is a diagram having eigenvectors corresponding to these eigenorder components, the eigen vectors having been rearranged on the basis of magnitude of their mean phase differences. That is, in terms of magnitude of the mean phase differences in the eigenvectors, the mean phase differences in the eigenvectors corresponding to the first, third, fifth, and sixth eigenorder components in FIG. 10 are larger than the mean phase differences in the eigenvectors corresponding to the other eigenorder components. By means of the extracting function 14b, the Doppler processing circuitry 14 selects, as an eigenvector to be reduced at Step S340, an eigenvector having a large mean phase difference. For example, in a case where N=4, by means of the extracting function 14b, the Doppler processing circuitry 14 selects, as eigenvectors to be reduced at Step S340, the top four eigenvectors in descending order of mean phase difference in FIG. 12, that is, the eigenvectors corresponding to the first, third, fifth, and sixth eigenorder components.

As illustrated in FIG. 7, at Step S340, by means of the extracting function 14b, the Doppler processing circuitry 14 removes the eigenvector components selected and thereby generates the second signal data string Y having the eigenvector components reduced therein, as expressed by Equation (3) below.

$$Y = \left(I - \sum_{k=1}^{K} a_k a_k^H\right) S \qquad (3)$$

In Equation (3), Y is the second signal data string Y, from which the eigenvector components selected at Step S330 have been removed, and S is the first signal data string S. Furthermore, k is an index for the eigenvector to be reduced and K is a value indicating the number of eigenvectors to be reduced. In addition, $a_k$ is a quantity corresponding to the eigenvalue and eigenvector corresponding to the k-th eigenorder component to be reduced, and I represents a unit matrix. That is, Equation (3) expresses that the second signal data string Y is obtained by subtraction of a component from the first signal data string S, the component being correlated with a predetermined eigenvector.

Subsequently, the Doppler processing circuitry 14 transmits the second signal data string Y to the image generator circuitry 15. At Step S400, the image generator circuitry 15 generates an ultrasound image on the basis of the second signal data string Y obtained from the Doppler processing circuitry 14.

As described above, in the first embodiment, principal component analysis of a first signal data string obtained from an echo signal is performed, and a second signal data string is extracted from the first signal data string by reducing a predetermined fundamental wave component in the first signal data string.

Clutter components are able to be reduced adequately with the imaging frame rate maintained high and the detectability of low-velocity components is thus able to be improved.

Second Embodiment

Figure 13:
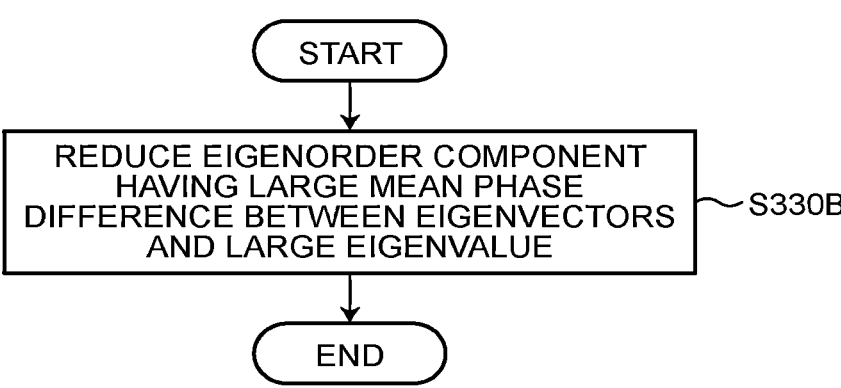
FIG. 13 is a flowchart illustrating a process at Step S330 in FIG. 7 in a second embodiment.

In the case described with respect to the first embodiment, at Step S330, the Doppler processing circuitry 14 selects, by means of the extracting function 14b, an eigenvector on the basis of mean phase differences in eigenvectors and reduces the eigenvector selected to thereby generate a second signal data string. However, embodiments herein are not limited to this case. In a second embodiment, the Doppler processing circuitry 14 extracts, by means of the extracting function 14*b*, a second signal data string on the basis of also an eigenvalue. That is, by means of the extracting function 14*b*, the Doppler processing circuitry 14 extracts the second signal data string on the basis of mean phase differences in eigenvectors and an eigenvalue of a correlation matrix R obtained as a result of principal component analysis. For example, by means of the extracting function 14*b*, the Doppler processing circuitry 14 executes a process of Step S330B, at Step S330, as illustrated in FIG. 13. That is, by means of the extracting function 14*b*, the Doppler processing circuitry 14 extracts a second signal data string Y by reducing an eigenorder component having a large mean phase difference in eigenvectors calculated at Step S320 and a large eigenvalue. That is, the second embodiment is a method of extracting the second signal data string Y by using both the method according to the first embodiment and an eigenvalue expansion filter.

As described above, in this second embodiment, the second signal data string Y is extracted by use of, not only the mean phase differences in eigenvectors, but also the eigenvalue of the correlation matrix obtained as a result of the principal component analysis. Clutter is thereby able to be reduced adequately in, for example, bloodstream imaging.

Modified Example of Second Embodiment

Figure 14:
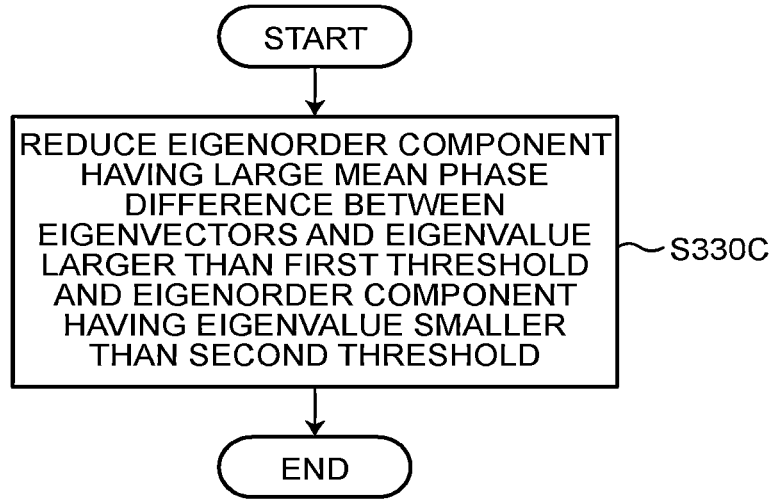
FIG. 14 is a flowchart illustrating a process at Step S330 in FIG. 7 in a modified example of the second embodiment.

In a case described with respect to a modified example of the second embodiment, an eigenorder component having a small eigenvalue is reduced in the second embodiment. For example, by means of the extracting function 14*b*, the Doppler processing circuitry 14 executes a process of Step S330C, at Step S330, as illustrated in FIG. 14. That is, by means of the extracting function 14*b*, the Doppler processing circuitry 14 extracts a second signal data string by reducing a signal component (a Doppler frequency component) having a mean phase difference in eigenvectors calculated at Step S330 larger than a predetermined threshold and having an eigenvalue larger than a first threshold, and a signal component (a Doppler frequency component) having an eigenvalue less than a second threshold. For example, in a case considered herein, ultrasound imaging is performed with a puncture needle enhanced, the puncture needle having been inserted in a subject. In this case, a bloodstream component may be reduced if the ultrasound imaging is specialized for imaging of the puncture needle. A bloodstream component is known to have a small eigenvalue. Therefore, by means of the extracting function 14*b*, the Doppler processing circuitry 14 reduces a fundamental wave component to reduce a clutter component by reducing a Doppler frequency component having a calculated mean phase difference in eigenvectors larger than the predetermined threshold and having an eigenvalue larger than the first threshold, reduces a bloodstream component by reducing a Doppler frequency component having an eigenvalue less than the second threshold, and thereby enables imaging with the puncture needle enhanced.

As described above, in the modified example of the second embodiment, a component having a small eigenvalue is additionally reduced. A bloodstream component is thereby able to be reduced and imaging is able to be performed with a puncture needle enhanced, for example.

Third Embodiment

Figure 15:
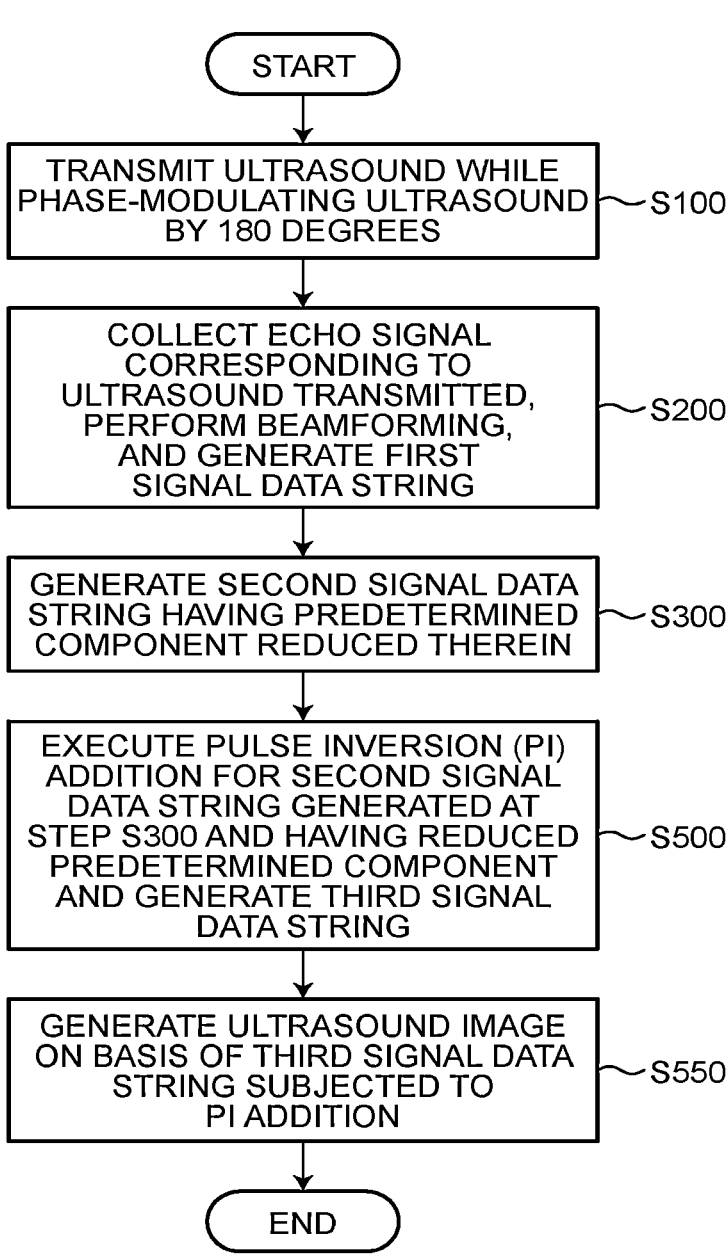
FIG. 15 is a flowchart illustrating a flow of a process implemented by an ultrasound diagnosis apparatus according to a third embodiment.

In the first embodiment, at Step S400, an ultrasound image is generated on the basis of a second signal data string generated at Step S300. In a third embodiment, an ultrasound image is generated after a pulse inversion (PI) addition process is performed for a second signal data string. FIG. 15 is a flowchart illustrating a flow of a process performed by an ultrasound diagnosis apparatus according to the third embodiment.

At Step S100, the transmitter and receiver circuitry 11 transmits ultrasound while phase-modulating the ultrasound by 180 degrees. At Step S200, the transmitter and receiver circuitry 11 receives an echo signal corresponding to the ultrasound transmitted, performs beamforming, and thereby generates a first signal data string S. At Step S300, the Doppler processing circuitry 14 generates, by means of the analyzing function 14*a* and the extracting function 14*b*, a second signal data string Y having a predetermined component reduced therein, from the first signal data string S. Processes from Step S100 to Step S300 are similar to those of the first embodiment and redundant description thereof will thus be omitted.

Subsequently, at Step S500, by means of the adding function 14*c*, the Doppler processing circuitry 14 executes pulse inversion (PI) addition for the second signal data string Y having the predetermined component reduced therein, the second signal data string Y having been generated at Step S300, and thereby generates a third signal data string. PI addition herein refers to addition of data of frames having phases different from each other by 180 degrees and this addition enables extraction of even-order harmonic components. That is, by means of the adding function 14*c*, the Doppler processing circuitry 14 performs addition for the second signal data string corresponding to the ultrasound transmissions having phases different from each other by 180 degrees to generate the third signal data string with the even-order harmonic components extracted therein. At Step S550, the image generator circuitry 15 generates an ultrasound image on the basis of the third signal data string generated at Step S500.

As described above, in the third embodiment, an ultrasound image is generated after PI addition for the second signal data string Y having the predetermined component reduced therein. Even-order harmonic components are thereby able to be extracted.

Fourth Embodiment

Figure 16:
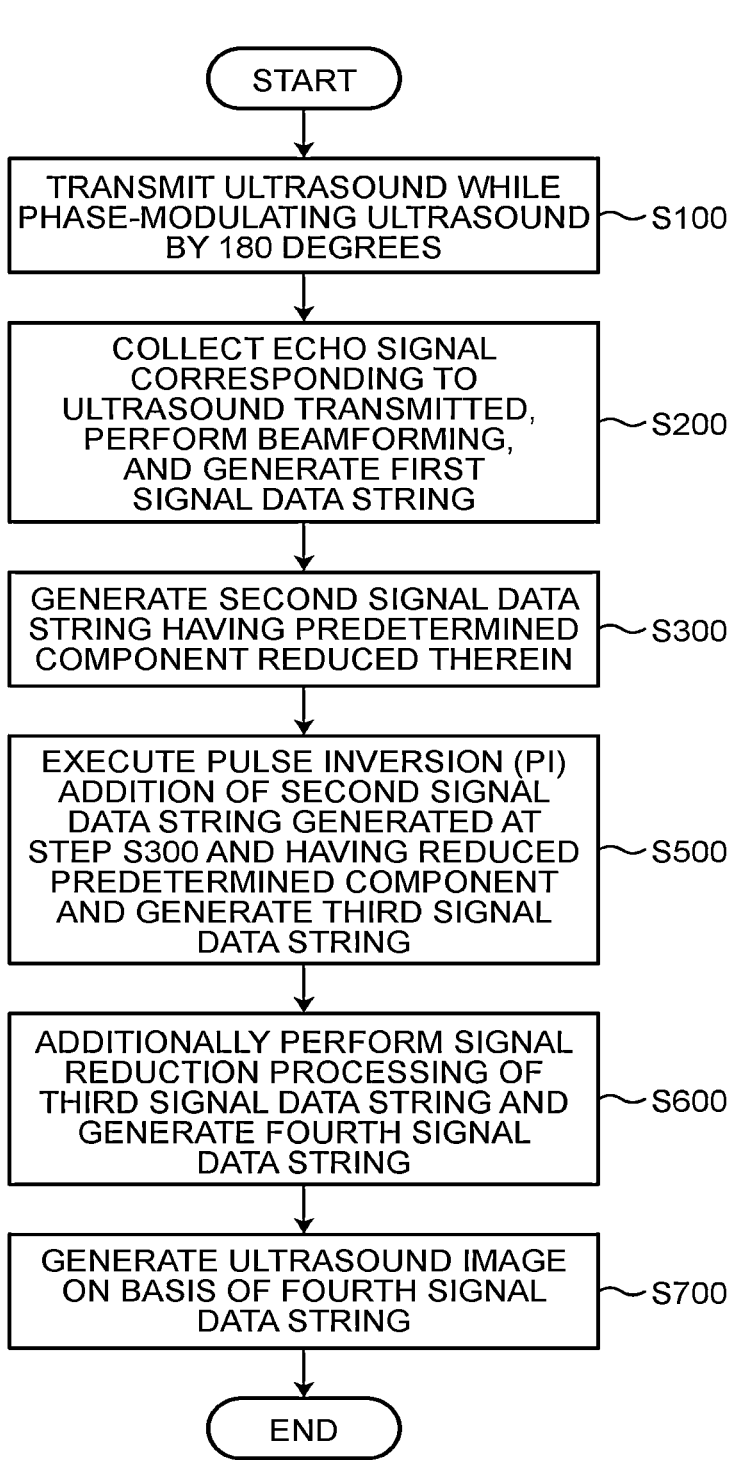
FIG. 16 is a flowchart illustrating a flow of a process implemented by an ultrasound diagnosis apparatus according to a fourth embodiment.

In a case described with respect to a fourth embodiment, a predetermined component is reduced by additionally performing filtering after PI addition in the third embodiment. FIG. 16 is a flowchart illustrating a flow of a process performed by an ultrasound diagnosis apparatus according to the fourth embodiment.

At Step S100, the transmitter and receiver circuitry 11 transmits ultrasound while phase-modulating the ultrasound by 180 degrees. At Step S200, the transmitter and receiver circuitry 11 receives an echo signal corresponding to the ultrasound transmitted, performs beamforming, and thereby generates a first signal data string S. At Step S300, the Doppler processing circuitry 14 generates, by means of the analyzing function 14*a* and the extracting function 14*b*, a second signal data string Y having a predetermined component reduced therein, from the first signal data string S. At Step S500, by means of the adding function 14*c*, the Doppler processing circuitry 14 executes PI addition for the second signal data string Y having the predetermined component reduced therein and having been generated at Step S300, to generate a third signal data string. Processes from Step S100 to Step S500 are similar to those of the first embodiment and redundant description thereof will thus be omitted.

Subsequently, at Step S600, the Doppler processing circuitry 14 performs, by means of the analyzing function 14a, principal component analysis of the third signal data string. By means of the extracting function 14b, the Doppler processing circuitry 14 reduces a predetermined Doppler frequency component from the third signal data string on the basis of at least one of an eigenvalue and an eigenvector obtained by the principal component analysis of the third signal data string, by performing a process similar to the process of Step S300, and thereby extracts a fourth signal data string. For example, the Doppler processing circuitry 14 extracts a bloodstream signal as the fourth signal data string by extracting, by means of the extracting function 14b, a harmonic component from the third signal data string.

Subsequently, at Step S700, the image generator circuitry 15 generates an ultrasound image on the basis of the fourth signal data string generated at Step S600.

As described above, in the fourth embodiment, filtering is performed in two stages of Step S300 and Step S600.

For example, at Step S300, by means of the extracting function 14b, the Doppler processing circuitry 14 may generate a second signal data string by cutting an eigenorder component having a large mean phase difference in eigenvectors, on the basis of mean phase differences in eigenvectors, and at Step S600, by means of the extracting function 14b, the Doppler processing circuitry 14 may generate a fourth signal data string by cutting an eigenorder component having a large eigenvalue by using an eigenvalue expansion filter. As described above, signal processing is able to be implemented more flexibly by combination, in two stages, of the method according to the first embodiment and an eigenvalue expansion filter.

Fifth Embodiment

In the case described with respect to the above described embodiments, the transmitter and receiver circuitry 11 performs ultrasound transmission by 180-degree phase modulation but embodiments are not limited to this case. A transmission and reception unit may execute so-called triplet scanning of transmitting ultrasound while phase-modulating the ultrasound by 120 degrees, to extract a third-order harmonic. Performing addition of three sets of data that have been phase-modulated by 120 degrees enables extraction of a third-order harmonic.

Figure 17:
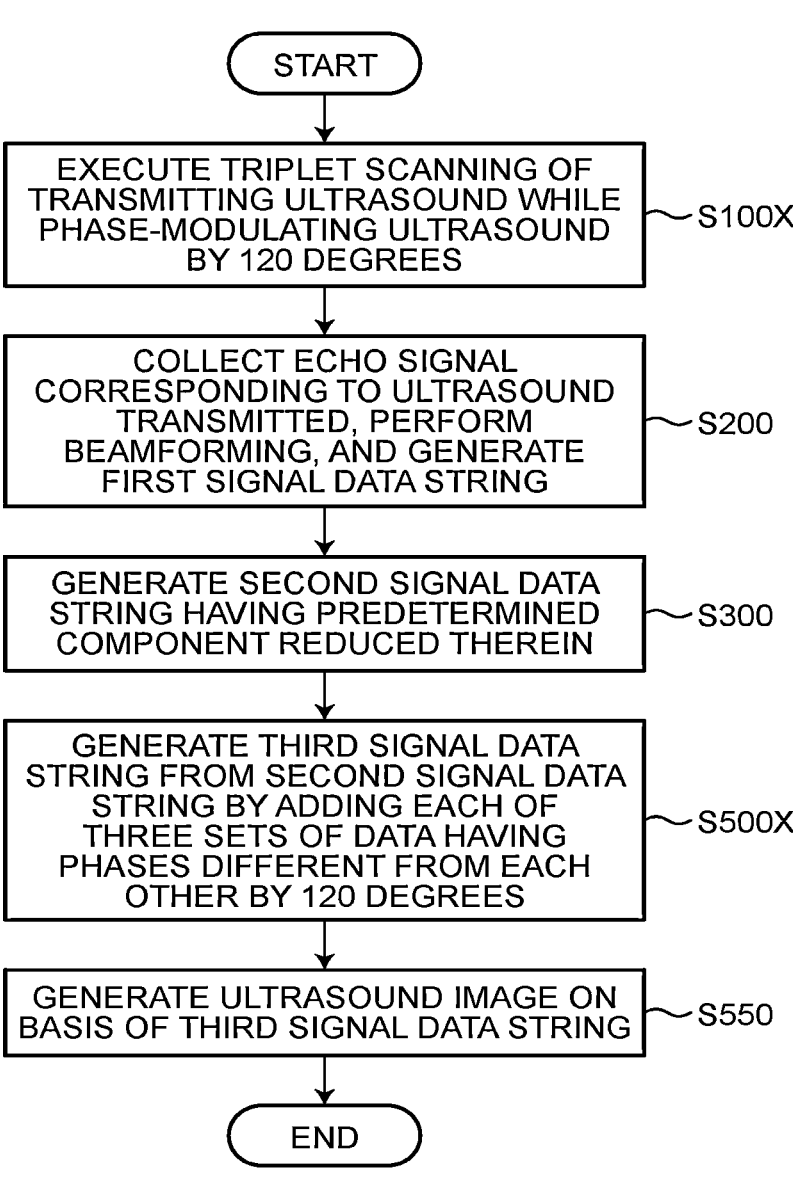
FIG. 17 is a flowchart illustrating a flow of a process implemented by an ultrasound diagnosis apparatus according to a fifth embodiment.

FIG. 17 illustrates an example of this process. FIG. 17 is a flowchart illustrating a flow of a process performed by an ultrasound diagnosis apparatus according to a fifth embodiment.

At Step S100X, the transmitter and receiver circuitry 11 executes triplet scanning of transmitting ultrasound while phase-modulating the ultrasound by 120 degrees. At Step S200, the transmitter and receiver circuitry 11 receives an echo signal corresponding to the ultrasound transmitted, performs beamforming, and thereby generates a first signal data string S. At Step S300, the Doppler processing circuitry 14 generates, by means of the analyzing function 14a and the extracting function 14b, a second signal data string Y having a predetermined component reduced therein, from the first signal data string S. At Step S500X, by means of the adding function 14c, the Doppler processing circuitry 14 generates a third signal data string from the second signal data string by adding each of three sets of data having phases different from each other by 120 degrees to the second signal data string Y having a predetermined component reduced therein and having been generated at Step S300. At Step S600, the image generator circuitry 15 generates an ultrasound image on the basis of the third signal data string.

Sixth Embodiment

Embodiments are not limited to the above described examples. Means disclosed in this specification are for separating predetermined Doppler frequency components in a signal data string by utilizing principal component analysis and in the first to fifth embodiments, the Doppler frequency components are generated just by transmission phase modulation. In a case described with respect to a sixth embodiment, an echo signal from a puncture needle vibrated to include a predetermined Doppler frequency is separated from a first signal data string and a signal resulting from the vibration of the puncture needle is extracted or reduced, by application of the first embodiment.

In this case, an ultrasound diagnosis apparatus according to the sixth embodiment further includes a vibrator to vibrate an object inserted in a subject, to which ultrasound is transmitted, for example, a puncture needle, at a certain frequency, and a needle connector to connect the vibrator and the object to each other, the vibrator and the needle connector not being illustrated in the drawings.

At Step S100, the transmitter and receiver circuitry 11 executes transmission of ultrasound while performing phase modulation. At Step S200, the transmitter and receiver circuitry 11 receives an echo signal corresponding to the ultrasound transmitted, performs beamforming, and thereby generates a first signal data string S. At Step S300, the Doppler processing circuitry 14 generates, by means of the analyzing function 14a and the extracting function 14b, a second signal data string Y from the first signal data string S, the second signal data string Y having a certain Doppler frequency component reduced therein or separated and extracted therefrom, the certain Doppler frequency component corresponding to vibration of a puncture needle. At Step S400, the image generator circuitry 15 generates an ultrasound image on the basis of the second signal data string Y.

Other Embodiments

Embodiments are not limited to the above described examples.

As to the process of extracting the second signal data string Y at Step S340 in the above described embodiments, a case where an eigenorder component having a large mean phase difference in eigenvectors is reduced has been described with respect to the first embodiment, and a case where a predetermined eigenorder component is reduced on the basis of also an eigenvalue has been described with respect to the second embodiment and the modified example of the second embodiment. However, embodiments are not limited to these cases.

For example, at Step S300, by means of the extracting function 14b, the Doppler processing circuitry 14 may extract a second signal data string on the basis of a correlation value between a unit vector corresponding to a transmission modulation phase and an eigenvector. Specifically, at Step S340, by means of the extracting function 14b, the Doppler processing circuitry 14 may select an eigenvector component to be removed, on the basis of a correlation value between a unit vector corresponding to a transmission modulation phase and an eigenvector. The unit vector corresponding to the transmission modulation phase is, for example, a unit vector n=cos θ+i sin θ corresponding to a transmission modulation phase θ.

Furthermore, in another example, at Step S300, by means of the extracting function 14b, the Doppler processing circuitry 14 may extract a second signal data string on the basis of the magnitude of a complex amplitude of an eigenvector. Specifically, at Step S330, by means of the extracting function 14b, the Doppler processing circuitry 14 may select an eigenvector component to be removed, on the basis of the magnitude of a complex amplitude of an eigenvector calculated at Step S320.

A case where the above described first signal data string S is data that have been sampled at temporally equal intervals has been described with respect to the embodiments, but embodiments are not limited to this case, and the first signal data string S may be data that have been sampled at unequal intervals.

At least one of the embodiments described above enables improvement in resolution of low-velocity components.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
an ultrasound probe;
transmitter and receiver circuitry configured to transmit ultrasound via the ultrasound probe and receive an echo signal corresponding to the transmitted ultrasound;
Doppler processing circuitry configured to perform principal component analysis of a first signal data string obtained from the echo signal and extract a second signal data string from the first signal data string by reducing a predetermined Doppler frequency component, based on at least one of an eigenvalue and an eigenvector obtained by the principal component analysis; and
processing circuitry configured to generate an ultrasound image using the ultrasound probe based on the second signal data string,
wherein the Doppler processing circuitry is further configured to extract the second signal data string based on a mean phase difference in the eigenvector.

2. The ultrasound diagnosis apparatus according to claim 1, wherein the transmitter and receiver circuitry is further configured to transmit the ultrasound in plural directions in a same phase that is a first phase in one frame and thereafter is configured to transmit the ultrasound in the plural directions in a second phase opposite to the first phase.

3. The ultrasound diagnosis apparatus according to claim 1, wherein the Doppler processing circuitry is further configured to extract the second signal data string based on a basis of a magnitude of a complex amplitude of the eigenvector.

4. The ultrasound diagnosis apparatus according to claim 1, wherein the Doppler processing circuitry is further configured to extract a bloodstream signal as the second signal data string, by extracting a harmonic component from the first signal data string.

5. The ultrasound diagnosis apparatus according to claim 1, wherein the first signal data string is data that have been sampled at unequal intervals.

6. The ultrasound diagnosis apparatus according to claim 1, further comprising:
a vibrator configured to vibrate, at a certain frequency, an object inserted in a subject where the ultrasound is transmitted, wherein the mean phase difference of the predetermined Doppler frequency component is larger than a predetermined threshold and the eigenvalue is larger than a first threshold and the predetermined Doppler frequency component eigenvalue is less than a second threshold, wherein the generated ultrasound image is an enhanced image of the object.

7. The ultrasound diagnosis apparatus according to claim 1, wherein
the transmitter and receiver circuitry is further configured to transmit the ultrasound while phase-modulating the ultrasound, and
the Doppler processing circuitry is further configured to extract the second signal data string by extracting a harmonic component from the first signal data string.

8. The ultrasound diagnosis apparatus according to claim 7, wherein the transmitter and receiver circuitry is further configured to transmit the ultrasound while phase-modulating the ultrasound by 120 degrees.

9. The ultrasound diagnosis apparatus according to claim 7, wherein
the transmitter and receiver circuitry is further configured to transmit the ultrasound while phase-modulating the ultrasound by 180 degrees, and
the Doppler processing circuitry is further configured to generate a third signal data string having an even-order harmonic component extracted therein, by adding the second signal data string corresponding to ultrasound transmission having phases different from each other by 180 degrees.

10. The ultrasound diagnosis apparatus according to claim 9, wherein
the Doppler processing circuitry is further configured to perform principal component analysis of the third signal data string, and is further configured to extract a fourth signal data string from the third signal data string by reducing a predetermined Doppler frequency component, based on at least one of an eigenvalue and an eigenvector obtained by the principal component analysis of the third signal data string.

11. The ultrasound diagnosis apparatus according to claim 10, wherein the Doppler processing circuitry is further configured to extract a bloodstream signal as the fourth signal data string, by extracting a harmonic component from the third signal data string.

12. The ultrasound diagnosis apparatus according to claim 1, wherein the Doppler processing circuitry is further configured to extract the second signal data string further based on the eigenvalue.

13. The ultrasound diagnosis apparatus according to claim 12, wherein the Doppler processing circuitry is further configured to extract the second signal data string by reducing: a Doppler frequency component having a mean phase difference larger than a predetermined threshold and the eigenvalue larger than a first threshold; and a Doppler frequency component having the eigenvalue less than a second threshold.

14. The ultrasound diagnosis apparatus according to claim 1, further comprising:

a vibrator configured to vibrate, at a certain frequency, an object inserted in a subject where the ultrasound is transmitted, wherein the Doppler processing circuitry is further configured to extract the second signal data string by reducing the certain Doppler frequency component.

15. The ultrasound diagnosis apparatus according to claim 14, wherein the object is a puncture needle, and the ultrasound diagnosis apparatus further comprises a needle connector configured to connect the vibrator and the object to each other.

16. An ultrasound diagnosis apparatus, comprising:

an ultrasound probe;

transmitter and receiver circuitry configured to transmit ultrasound via the ultrasound probe and receive an echo signal corresponding to the transmitted ultrasound;

Doppler processing circuitry configured to perform principal component analysis of a first signal data string obtained from the echo signal and extract a second signal data string from the first signal data string by reducing a predetermined Doppler frequency component, based on at least one of an eigenvalue and an eigenvector obtained by the principal component analysis, and processing circuitry configured to generate an ultrasound image using the ultrasound probe based on the second signal data string, wherein the Doppler processing circuitry is further configured to extract the second signal data string based on a correlation value between (1) a unit vector n=cos θ+i sin θ corresponding to a transmission modulation phase, and (2) the eigenvector.

17. An ultrasound diagnosis method, including:

transmitting ultrasound via an ultrasound probe and receiving an echo signal corresponding to the transmitted ultrasound;

performing principal component analysis of a first signal data string obtained from the echo signal;

extracting a second signal data string from the first signal data string by reducing a predetermined Doppler frequency component, based on a mean phase difference in an eigenvector obtained by the principal component analysis; and generating an ultrasound image using the ultrasound probe based on the second signal data string.

* * * * *